United States Patent [19]

Tanida et al.

[11] Patent Number: 4,540,517

[45] Date of Patent: Sep. 10, 1985

[54] ANTIBIOTIC TAN-420

[75] Inventors: Seiichi Tanida, Nagaokakyo; Masayuki Muroi, Suita; Toru Hasegawa, Kawanishi, all of Japan

[73] Assignee: Takeda Chemical Industries, Ltd., Osaka, Japan

[21] Appl. No.: 557,364

[22] Filed: Dec. 2, 1983

[30] Foreign Application Priority Data

Dec. 3, 1982 [JP] Japan .................... 57-212974

[51] Int. Cl.³ .................... C07D 225/06; C12P 13/00; C12R 1/365
[52] U.S. Cl. .................... 260/239.3 B; 435/128; 435/872
[58] Field of Search .................... 260/239.3 B

[56] References Cited

U.S. PATENT DOCUMENTS 4,187,292  2/1980  Higashide et al. .................. 244/122
4,421,687 12/1983  Hasegawa et al. ........... 260/239.3 B
4,421,688 12/1983  Muroi et al. ................ 260/239.3 B

OTHER PUBLICATIONS

Chemical Abstracts, vol. 97, (1982) Item 106668(s) Abstracting Hatano et al., "Agrio. Biol. Chem." (1982), vol. 46, No. 6, pp. 1699–1702.
Chemical Abstracts, vol. 98, (198) Item 83315(d) Abstracting Ono et al., "Gann" (1982), vol. 73, No. 6, pp. 938–944.
Muroi et al., *Tetrahedron Letters*, vol. 21, pp. 309–312 (1980).
Muroi et al., *Tetrahedron*, vol. 37, pp. 1123–1130 (1981).
Sasaki et al., *Journal of the American Chemical Society*, vol. 92, pp. 7591–7593 (1970).
Johnson et al., *Journal of the American Chemical Society*, vol. 96, pp. 3316–3317 (1974).
Omura et al., *Tetrahedron Letters*, No. 44, pp. 4323–4326 (1979).
Iwai et al., *The Journal of Antibiotics*, vol. 33, pp. 1114–1119 (1980).

*Primary Examiner*—Robert T. Bond
*Attorney, Agent, or Firm*—Wenderoth, Lind & Ponack

[57] ABSTRACT

A compound of the formula:

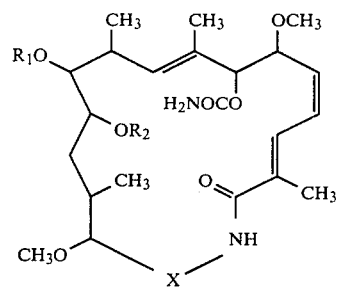

wherein $R_1$ and $R_2$ are the same or different and each represents hydrogen or methyl and X is

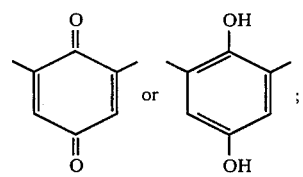

provided that when $R_1$ is hydrogen, $R_2$ is hydrogen or methyl and X is

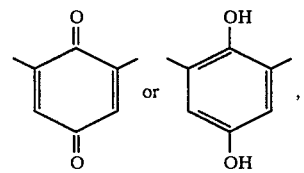

and when $R_1$ is methyl, $R_2$ is methyl and X is

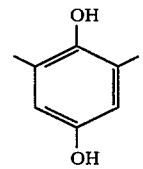

is produced by cultivating a a microorganism belonging to the genus Streptomyces in a culture medium. Said compound is useful as an antimicrobial agent and so forth.

6 Claims, No Drawings

ANTIBIOTIC TAN-420

The present invention reltates to Antibiotic TAN-420, its production and producer.

In search of new antibiotics, the present inventors isolated a large variety of microorganisms from soil and performed screenings for identifying the antibiotics which the microorganisms produce. The research resulted in the finding that cultures of certain strains of microorganisms so isolated elaborate antibiotics which are active against gram-positive bacteria, fungi and protozoae. The inventors isolated and purified those antibiotics, studied their properties, found that they are novel antibiotics, and named them Antibiotic TAN-420A, B, C, D and E. It was further found that these microorganisms belong to the genus Streptomyces, that said antibiotics are accumulated in a culture medium by cultivating these microorganisms in a suitable culture medium, and that the particular antibiotics belong to the ansamycin antibiotics. These findings prompted further research which has culminated in the development of the present invention.

The present invention is directed to (1) compounds having the formula:

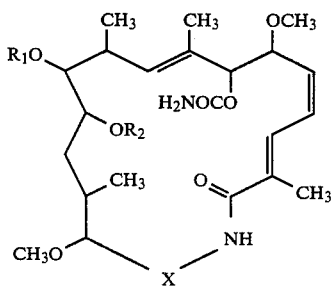

wherein $R_1$ and $R_2$ are the same or different and each represents hydrogen or methyl and X is

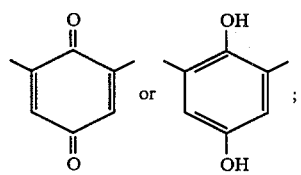

provided that when $R_1$ is hydrogen, $R_2$ is hydrogen or methyl and X is

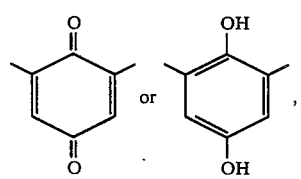

and when $R_1$ is methyl, $R_2$ is methyl and X is

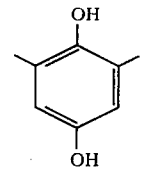

(2) a method of producing the compounds [I], which comprises cultivating a microorganism of the genus Streptomyces which is capable of elaborating at least one of said compounds in a culture medium and harvesting the same compound or compounds thus elaborated and accumulated in the medium, and (3) a biologically pure culture of a microorganism belonging to the genus Streptomyces having the identifying characteristics of FERM BP-376 or BP-375, said culture being capable of producing in a culture medium containing assimilable carbon and digestible nitrogen sources, a recoverable amount of the compound [I].

In this specification, the compounds of the formula [I] will be referred to briefly as follows.

| Compound | $R_1$ | $R_2$ | X |
|---|---|---|---|
| TAN-420A | H | H | ![OH-phenol-OH] |
| TAN-420B | H | H | ![quinone] |
| TAN-420C | H | $CH_3$ | ![OH-phenol-OH] |
| TAN-420D | H | $CH_3$ | ![quinone] |
| TAN-420E | $CH_3$ | $CH_3$ | ![OH-phenol-OH] |

In this specification, Antibiotic TAN-420A will sometimes be referred to briefly as TAN-420A or simply as A; Antibiotic TAN-420B as TAN-420B or B; Antibiotic TAN-420C as TAN-420C or C; Antibiotic TAN-420D as TAN-420D or D; and Antibiotic TAN- 420E as TAN-420E or E. Moreover, for convenience Antibiotic TAN-420A, B, C, D and E will sometimes be independently or generically referred to as Antibiotic TAN-420.

Furthermore, in this specification, any and all microorganisms of the genus Streptomyces which are capable of producing at least one of the compounds [I] will sometimes be referred to as "TAN-420 producing strain".

As examples of the TAN-420 producing strain, there may be mentioned Streptomyces sp. No. C-41206 (hereinafter referred to briefly as Strain C-41206) which the present inventors isolated from a soil sample collected at Tsukechi River, a tributary of Kiso River, in Gifu Prefecture, Japan and Streptomyces sp. No. C-41125 (hereinafter referred to briefly as Strain C-41125) which was isolated from a soil sample collected at Irako, Atsumi-gun, Aichi Prefecture, Japan.

The following is a description of Strain C-41206 based on results of the identification study conducted in accordance with the method of Shirling and Gottlieb [International Journal of Systematic Bacteriology 16, 313–340 (1966)].

Characteristics of Strain C-41206

(1) Morphology:

On various solid media, Strain C-41206 produces gray aerial mycelia, which are spiral at terminals. A large number of spores are formed in chains at the terminals of aerial mycelium but none of sporangium, myxomonade and sclerotium are observed. The spores are cylindrical or ellipsoidal and measure 0.7 to 0.9 μm by 1 to 1.2 μm, with generally smooth surfaces.

(2) Cultural characteristics:

This strain gives good growth on many taxonomic media, producing an abundant gray aerial mycelium. The substrate mycelium is light yellow to light brown, and a brown soluble pigment is produced on several kinds of solid media. The aerial mycelium becomes moistened on maturation.

The growth and physiological characteristics and the carbon source utilization of this strain are shown below (Tables 1 to 3).

TABLE 1

Characteristics of Strain C-41206 on Taxonomic Media (a) Sucrose nitrate agar:
  Growth (hereinafter, G): moderate, light cream-color (2 ca)
  Aerial mycelium (hereinafter, A): moderate, powdery, gray (5 fe)
  Soluble pigment (hereinafter, P): none
(b) Glucose asparagine agar:
  G: moderate, light wheat-color (2 ea)
  A: abundant, gray (5 fe)
  P: none
(c) Glycerin asparagine agar:
  G: moderate, light wheat-color (2 ea)
  A: abundant, gray (5 fe)
  P: none
(d) Nutrient agar:
  G: moderate, light wheat-color (2 ea)
  A: sparse, light cream-color (2 cb)
  P: none
(e) Calcium malate agar:
  G: moderate, cream-color (2 ca)
  A: moderate, light brown (3 cd)
  P: none
(f) Yeast extract malt extract agar:
  G: good, light yellowish brown (1 la)
  A: abundant, gray (5 fe)
  P: moderate, brown (3 li)
(g) Oatmeal agar:
  G: moderate, light yellow (1 ca)
  A: abundant, gray (5 fe)
  P: none
(h) Inorganic salt starch agar:
  G: good, wheat-color (2 ea)
  A: abundant, gray (5 fe)
  P: moderate, brown (3 li)
(i) Peptone yeast extract iron agar:
  G: poor, wheat-color (2 ea)
  A: sparse, white
  P: none
(j) Tyrosine agar:
  G: moderate, yellowish brown (3 gc)
  A: abundant, gray (3 fe)
  P: moderate, yellowish brown (3 lg)

TABLE 2

| Physiological Characteristics of Strain C-41206 | |
|---|---|
| Temperature for growth: | 18 to 34° C. |
| Optimal temperature for growth: | 20 to 33° C. |
| Gelatin: | liquefied |
| Starch: | Hydrolyzed |
| Nitrates: | not reduced |
| Milk: | peptonized |
| Milk: | not coagulated |
| Melanoid pigments: | not produced |

TABLE 3

| Carbon Source Utilization of Strain C-41206 | |
|---|---|
| Glycerin | ++ |
| Sorbitol | + |
| Inositol | ++ |
| Mannitol | ++ |
| Xylose | ++ |
| Arabinose | + |
| Galactose | ++ |
| Glucose | ++ |
| Fructose | ++ |
| Mannose | ++ |
| Maltose | ++ |
| Sucrose | ++ |
| Lactose | ++ |
| Trehalose | ++ |
| Rhamnose | ++ |
| Melibiose | ++ |
| Soluble starch | ++ |
| Control | ± |

Notes:
++: well utilized; +: utilized; ± slightly utilized.
The above characteristics were determined by the method of Pridham and Gottlieb [Journal of Bacteriology 56, 107 (1948)].

(3) Cell composition:

Using a modified ISP No. 1 medium, Strain C-41206 was shake-cultured at 28° C. for 66 to 90 hours to harvest cells in the stationary phase of growth. Analysis of the cells for diaminopimelic acid by the method of Backers et al. [Applied Microbiology 12, 421 (1964)] showed that the same acid is the LL form.

The above characteristics of Strain C-41206 were compared with the descriptions in S. A. Waksman: The Actinomycetes Vol. 2, The William and Wilkins Company (1961) and R. E. Buchanan and N. E. Gibbons (ed.): Bergey's Manual of Determinative Bacteriology, 8th Edition, 1974.

As mentioned hereinbefore, Strain C-41206 is characterized in that (1) it produces a gray aerial mycelium, the terminal ends of which are spiral, (2) its mature aerial mycelium is moist, (3) spore surfaces are generally smooth, (4) it does not produce melanoid pigments, and (5) its cells contain the LL form of diaminopimelic acid. These characteristics are very close to those of *Streptomyces hygroscopicus* (Jensen) Waksman and Henrici (1948) which is a Streptomyces organism. However, Strain C-41206 is different from the above strain in that the former utilizes inositol and raffinose well, produces a brown pigment on various solid media, and produces Antibiotic TAN-420.

However, since Strain C-41206 has much in common with *Streptomyces hygroscopicus*, it was considered appropriate to classify the strain as a sub-species of *Streptomyces hygroscopicus*. Accordingly, the present inventors named it *Streptomyces hygroscopicus* subsp. tsukechiensis No. C-41206. this name was adopted based on the name of the place where it was obtained (Tsukechi River, a tributary of Kiso River, in Gifu Prefecture, Japan).

The following description of Strain C-41125 is based on the studies conducted in accordance with the methods described in International Journal of Systematic Bacteriology 16, 313–340 (1966).

Characteristics of Strain C-41125

(1) Morphology:

On various solid media, this strain produces a gray aerial mycelium, the terminal ends of which are spiral. A large number of spores are formed in chains at the terminals of aerial mycelium, and none of sporandium, myxomonade and sclerotium are observed. The spore is cylindrical or ellipsoidal and measures 0.7 to 0.9 μm by 1 to 1.2 μm, with a generally smooth surface.

(2) Cultural characteristics on taxonomic media:

On many taxonomic media this strain gives good growth and produces an abundant gray aerial mycelium. The substrate mycelium is light yellow to yellowish brown and there is substantially no production of soluble pigments. The aerial mycelium becomes moistened on maturation.

The cultural characteristics of this strain on various media are shown in Table 4.

TABLE 4

Characteristics of Strain No. C-41125 on taxonomic media (a) Sucrose nitrate agar:
 Growth (hereinafter, G): moderate, white
 Aerial mycelium (hereinafter, A): moderate, powdery, light gray (3 fe)
 Soluble pigment (hereinafter, P): none
(b) Glucose asparagine agar:
 G: moderate, light wheat-color (2 ea)
 A: abundant, light gray (3 fe)
 P: none
(c) Glycerol asparagine agar:
 G: moderate, light wheat-color (2 ea)
 A: moderate, light cream-color (2 dc)
 P: none
(e) Nutrient agar:
 G: moderate, light wheat-color (2 ea)
 A: sparse, light cream-color (2 cb)
 P: none
(e) Calcium malate agar:
 G: moderate, cream-color (2 ca)
 A: sparse, white
 P: none
(f) Yeast extract malt extract agar:
 G: good, light yellowish brown (3 la)
 A: abundant, gray (5 fe)
 P: sparse, light yellow
(j) Oatmeal agar:
 G: moderate, light yellow (1 ca)
 A: abundant, gray (5 fe)
 P: none
(h) Inorganic salt starch agar:
 G: good, wheat-color (2 ea)
 A: abundant, gray (5 fe)
 P: none
(i) Peptone yeast extract iron agar:
 G: poor, wheat-color (2 ea)
 A: sparse, white
 P: none
(j) Tyrosine agar:
 G: moderate, yellowish brown (3 gc)
 A: abundant, gray (3 fe)
 P: sparse, yellowish brown The physiological characteristics, carbon source utilization spectrum and cellular composition of Strain C-41125 are identical with those of Strain C-41125.

Thus, described hereinbefore, Strain C-41206 is characterized in that (1) it produces a gray aerial mycelium, (2) its mature aerial mycelium is moistened, (3) its spore has a smooth surface, (4) it does not produce a melanoid pigment, and (5) its cells contain the LL form of diaminopimelic acid. These characteristics are very close to those of *Streptomyces hygroscopicus* (Jensen) Waksman and Henrici (1948) which belongs to the genus Streptomyces. However, the present strain is different from the latter in that the former utilizes inositol and raffinose well and produces Antibiotics TAN-420. However, since Strain C-41125 has much in common with *Streptomyces hygroscopicus*, it was considered appropriate to classify it as a strain of *Streptomyces hygroscopicus*. Accordingly, the strain was named *Streptomyces hygroscopicus* No. C-41125.

Strain C-41206 and Strain C-41125 have been deposited at the Institute for Fermentation, Osaka (IFO), Japan and at the Fermentation Research Institute, Agency of Industrial Science and Technology, Ministry of International Trade and Industries (FRI), Japan. The deposit dates and numbers are as follows.

| Strain | Culture collection | Date of deposit | Deposit No. |
|---|---|---|---|
| C-41206 | IFO | Sept. 27, 1982 | IFO 14208 |
| C-41206 | FRI | Nov. 11, 1982 | FERM P-6790 |
| C-41125 | IFO | Sept. 27, 1982 | IFO 14207 |
| C-41125 | FRI | Dec. 1, 1982 | FERM P-6810 |

The Strains C-41206 and C-41125, which were deposited at FRI, the deposits being converted to deposits under the Budapest Treaty, have been stored at FRI under the accession numbers of FERM BP-376 and FERM BP-375, respectively.

Microorganisms of the genus Streptomyces generally are liable to vary their characteristics and can be easily caused to undergo mutation by artificial treatments with for example ultraviolet light, X-rays or other radiation, or by means of a mutagen. Such mutants can also be used for the purposes of the present invention insofar as they are capable of producing TAN-420.

The medium for use in the cultivation of the TAN-420 producing strain in accordance with the present invention may optionally be a liquid medium or a solid medium, although the former is more convenient. While the cultural method may optionally be surface culture or shake culture, submerged aerobic culture is advantageous. For the preparation of medium, carbon sources which are assimilable to the TAN-420 producing strain, such as starch, glucose, dextrin, glycerin, sucrose, n-paraffin, alcohols (e.g. methanol), organic nitrogen sources such as corn steep liquor, soybean meal, cottonseed meal, peptone, meat extract, etc., and inorganic nitrogen sources such as ammonium chloride, ammonium sulfate, ammonium nitrate, urea, etc. can be employed. If necessary, there may also be added to the medium, in the appropriate amounts, inorganic salts such as salts of sodium, potassium, magnesium, calcium or phosphorus, heavy metal salts such as salts of iron, manganese, zinc, cobalt, copper, nickel or the like, antifoams such as soybean oil, lard oil, chicken oil, silicone oil, Actcol (Takeda Chemilcal Industries, Ltd., Japan), etc. In liquid culture, the pH of the medium is preferably maintained near neutral, i.e. pH 6 to 8. The preferred temperature and time of incubation are 24° to 30° C. and 90 to 140 hours, respectively.

The time-course change of the antibiotic titer with the progress of cultivation can be monitored by a bioassay method using *Candida albicans* IFO 0583 and *Tetrahymena pyriformis* W [Tanida et al., The Journal of Antibiotics 33, 199 (1980)].

For recovering at least one TAN-420 antibiotic species produced and accumulated in the culture, conventional methods of isolating and purifying similar neutral and liposoluble microbial metabolites can be used in suitable combinations. For example, methods of utilizing the differential solubility with respect to impurity and adsorption chromatography using various adsorbents such as nonionic high-porous resins, silica gel, alumina, etc. can be used independently or in a suitable combination.

While generally Antibiotic TAN-420 is predominantly contained in the liquid fraction of the cultured broth, it can also be harvested from the microbial cells. Extraction from the cells can be carried out using a water-miscible organic solvent such as lower alcohols (e.g. methanol, ethanol, etc.), ketones (e.g. acetone, methyl ethyl ketone, etc.), etc. or a mixture of such organic solvent or solvents with water.

Extraction may also be accomplished by using an organic solvent immiscible with water, e.g. ethyl acetate and other esters. Moreover, extraction may also be carried out by adding a water-miscible organic solvent, such as methanol, acetone, etc., to the culture.

For recovering Antibiotic TAN-420 from the culture filtrate or supernatant, an extraction procedure using an organic solvent immiscible with water, such as fatty acid esters (e.g. ethyl acetate, butyl acetate, etc.), alcohols (e.g. butanol, etc.), halogenated hydrocarbon (e.g. chloroform, methylene chloride, etc.), or ketones (e.g. methyl ethyl ketone) can be employed. The organic solvent extract is washed with water and concentrated, followed by addition of a nonpolar organic solvent such as n-hexane, whereupon a crude product is obtained. When only one species of Antibiotic TAN-420 occurs predominantly, it may be isolated as crystals by the above organic solvent extraction and concentration procedure.

For recovering Antibiotic TAN-420 from the culture filtrate, adsorption on a nonionic high-porous resin such as Diaion HP-10 (Mitsubishi Chemical Industries Ltd., Japan) and elution with an aqueous alcohol or aqueous ketone may also be utilized.

When the crude product obtained as above from the culture by extraction, concentration and other procedures is a mixture of Antibiotic TAN-420 compounds, various kinds of adsorption chromatography can be utilized for separation of the species. The adsorbent may be the conventional material such as silica gel, alumina, nonionic high porous resin, etc.

When silica gel is used as said adsorbent, desorption with a combination of polar and nonpolar organic solvents, such as ethyl acetate and n-hexane or methanol and chloroform can be utilized with advantage. Thus, after an initial development with a nonpolar solvent, elution is carried out with an increasing proportion of a polar solvent, whereby the species are separated. When the crude product contains a plurality of species as well as much impurity, the desired single species can be isolated by varying the combination of such organic solvents and repeating the chromatography.

In some cases, high performance liquid chromatography on an adsorbent such as silica gel or a reverse-phase chromatographic support such as $\mu$Bondapak $C_{18}$ (Waters Associates, U.S.A.) can also be utilized.

Antibiotic TAN-420 consists of the quinone form (TAN-420B, D and TAN-420F mentioned hereinafter) and the hydroquinone form (TAN-420A, C and E) which are intertransformable. That is to say, TAN-420B and A are intertransformable. TAN-420D and C are intertransformable and TAN-420F and E are intertransformable. Therefore, in purifying it, if they are oxidized or reduced to either the quinone form or the hydroquinone form, the variety of species is halved, thus assisting in the purification procedure.

For such oxidation, the method generally used for oxidizing a hydroquinone compound can be utilized. Examples of the oxidizng agent therefor include ferric chloride, ferric sulfate, potassium ferricyanide, oxygen (air), silver oxide, etc. The reaction solvent may be any solvent that does not interfere with the reaction and may for example be an ester (e.g. ethyl acetate, etc.), a ketone (e.g. acetone, etc.) or water, although a mixture of such solvents may also be used. Further, a biphasic solvent such as a combination of water with a water-immiscible organic solvent may also be used with advantage. The amount of such oxidizing agent is about 1 to 200 molar equivalents relative to each equivalent of the substrate compound. While the reaction temperature is substantially optional, the reaction is generally carried out at about 0° to 40° C. and more commonly at room temperature. The reaction time depends on the oxidizing agent and reaction temperature used but the reaction can be easily carried to completion generally in about 30 seconds to about 24 hours.

For said reduction, the method commonly used for reducing a quinone compound can be utilized. The reducing agent for the purpose may for example be sodium hydrosulfite, sodium hydrogen sulfite, sodium borohydride or the like. The reaction solvent may be any solvent that does not interfere with the reaction. Thus, for example, esters such as ethyl acetate, etc., alcohols such as methanol, ethanol, etc., and water may be mentioned, although a mixture of such solvents may also be employed. Furthermore, a biphasic solvent such as a combination of water with a water-immiscible organic solvent (e.g. ethyl acetate/water) can be utilized with advantage. The amount of such reducing agent is generally about 1 to 200 molar equivalents relative to each equivalent of the substrate compound. The reaction is generally carried out at about 0° to 40° C., and more commonly at room temperature. Depending on the species of reducing agent and reaction temperature selected, the reaction can be successfully carried to completion in about 30 seconds to about 24 hours.

As to the silica gel chromatography for purification of the desired compound, such purification is generally carried out on the quinone form but there are cases in which purification on the hydroquinone form is more advantageous, and the species can be separated by utilizing either the oxidation or the reduction procedure according to the relative proportions of the species in the mixture and the amount and kind of impurity.

Each of the species can be isolated as crystals or amorphous powders from an organic solvent such as ethyl acetate, methanol, chloroform, methylene chloride, etc., a mixture of such a solvent with n-hexane or diethyl ether, or a mixture of methanol, ethanol or the like with water.

The physiochemical properties of Antibiotic TAN-420A, B, C, D and E obtained in Example 1 which appears hereinafter are shown in Tables 5 to 8.

TABLE 7

|  | TAN-420A | TAN-420B |
|---|---|---|
| Thin layer chromatography (Rf) | | |
| chloroform-methanol (9:1) | 0.17 | 0.57 |
| ethyl acetate-n-hexane (4:1) | 0.03 | 0.41 |

TABLE 8

|  | TAN-420E |
|---|---|
| Form | Colorless crystal |
| Melting point | 166 to 167° C. |
| Specific rotation $[\alpha]_D^{25}$ | +38.6° (c = 0.5, MeOH) |
| Elemental analysis (%) | |
| C | 59.10 |
| H | 7.99 |
| N | 4.60 |
| Ultraviolet absorption spectrum $\lambda_{max}^{MeOH}$ | 252 nm ($E_{1\ cm}^{1\%}$ 323), 307 nm ($E_{1\ cm}^{1\%}$ 77) |
| Infrared absorption spectrum (main peak) $\nu_{max}^{KBr}$ | 1715, 1640, 1600, 1530, 1470, 1380, 1315, 1190, 1155, 1105, 1065, 1045, 895, 865, 780 |
| Thin layer chromatography Rf value | chloroform-methanol (9:1) 0.53 / ethyl acetate n-hexane (4:1) 0.19 |

Based on the above physiochemical properties, $^1$H-NMR and $^{13}$C-NMR spectra and other data, the chemical structure of Antibiotic TAN-420 according to the

TABLE 5

|  | TAN-420C | TAN-420D |
|---|---|---|
| Melting point | 158 to 159° C. | >300° C. |
| Form | Colorless crystal | Yellow crystal |
| Specific rotation $[\alpha]_D^{25}$ | +51.6° (MeOH) | +219.0° (CHCl$_3$) |
| Elemental analysis (%) | | |
| C | 60.15 | 62.00 |
| H | 7.11 | 7.35 |
| N | 4.56 | 5.02 |
| Mass spectrum (M$^+$) | m/z 562 | m/z 560 |
| Ultraviolet absorption spectrum $\lambda_{max}^{MeOH}$ ($E_{1cm}^{1\%}$) | 252 nm (315), 307 nm (78) | 271 nm (499), 396 nm (48.1) |
| Infrared absorption spectrum (main peak) $\nu_{max}^{KBr}$ cm$^{-1}$ | 1720, 1660, 1600, 1535, 1460, 1380, 1320, 1235, 1195, 1160, 1095, 1065, 965, 865, 780 | 1735, 1705, 1670, 1650, 1610, 1500, 1460, 1375, 1320, 1285, 1265, 1255, 1205, 1135, 1100, 1055, 1000, 960, 940, 910, 870, 835, 780, 680 |
| Thin layer chromatography (Rf) (Merck, TLC glass plate, silica gel F$_{254}$) | | |
| chloroform-methanol (9:1) | 0.52 | 0.70 |
| ethyl acetate-n-hexane (4:1) | 0.18 | 0.34 |

TABLE 6

|  | TAN-420B | |
|---|---|---|
|  | α Crystal | β Crystal |
| Melting point | 219 to 220° C. | >300° C. |
| Specific rotation $[\alpha]_D^{25}$ | +58.6° (c = 0.5, DMSO) | +56.4° (c = 0.5 DMF) |
| Form | Yellow crystal | Yellow crystal |
| Elemental analysis (%) | | |
| C | 60.84 | 59.71 |
| H | 7.06 | 7.08 |
| N | 4.94 | 5.08 |
| Mass spectrum (M$^+$) | m/z 546 | m/z 546 |
| Ultraviolet absorption spectrum $\lambda_{max}^{MeOH}$ ($E_{1cm}^{1\%}$) | 270 nm (397) 394 nm (46.2) | 270 nm (355) 394 nm (42.8) |
| Infrared absorption spectrum (main peak) $\nu_{max}^{KBr}$ cm$^{-1}$ | 1720, 1670, 1655, 1610, 1505, 1460, 1385, 1330, 1295, 1210, 1180, 1140, 1105, 1070, 985, 910, 880, 780 | 1730, 1700, 1675, 1655, 1630, 1605, 1505, 1460, 1380, 1330, 1290, 1260, 1205, 1170, 1140, 1115, 1050, 980, 905, 875, 785, 700 | present invention was presumed to be as indicated by the formula [I]. As to TAN-420B, there have been obtained two kinds of crystals (α and β) which are different from each other in melting point, elemental analysis and infrared absorption spectrum.

Based on the above physical, chemical and other data, all the compounds of TAN-420 are considered to be novel.

Antibiotic TAN-420 has antibacterial, antifungal and antiprotozoal activities, and in view of its cytocidal effects on tumor cells, is expected to have anti-tumor activity as well. And also TAN-420 is expected to have herbicidal activity. Moreover, TAN-420 is also of value as an intermediate for the production of useful derivatives.

The biological activity and acute toxicity data on Antibiotic TAN-420 are shown below.

Antimicrobial activity

The antimicrobial activity of Antibiotic TAN-420B, C, D and E was assayed by the agar dilution method using Typticase soy agar (Baltimore Biological Laboratories, U.S.A.) as the test medium. The results are shown in Table 9.

TABLE 9

| | Minimal inhibitory concentration (µg/ml) TAN-420 | | | |
|---|---|---|---|---|
| Test microorganism | B | C | D | E |
| Escherichia coli K12 | >100 | >100 | >100 | >100 |
| Pseudomonas aeruginosa IFO 3080 | >100 | >100 | >100 | >100 |
| Bacillus subtilis PCI 219 | >100 | >100 | >100 | 100 |
| B. brevis IFO 3331 | 50 | 50 | 50 | 50 |
| B. cereus IFO 3514 | 100 | 100 | 100 | 100 |
| B. pumilus IFO 3813 | 100 | 100 | 100 | 100 |
| B. megaterium IFO 12108 | 100 | 100 | 100 | 50 |
| Staphylococcus aureus FDA 209P | 100 | 100 | 100 | 100 |
| Micrococcus flavus IFO 3242 | 25 | 25 | 25 | 50 |

In the liquid dilution assay of antiprotozoal activity of Antibiotic TAN-420 with *Tetrahymena pyriformis* W as the test microorganism, TAN-420B, C, D and E showed minimal inhibitory concentrations of 40, 10, 4 and 2 µg/ml, respectively. The antimicrobial activity of TAN-420A is thus considered to be of the same order as that of TAN-420B.

As regards the acute toxocity of Antibiotic TAN-420 (mouse, intraperitoneal), the LD$_{50}$ value of TAN-420C was 200 to 400 mg/kg, that of TAN-420D was 100 mg/kg, and that of TAN-420E was 50 mg/kg. It is therefore, considered that the toxicity of Antibiotic TAN-420 is low.

As aforementioned, Antibiotic TAN-420 can be used as an antimicrobial agent. By way of example, TAN-420 can be made into an ethanol-containing aqueous solution (ethanol content about 5 to 50 v/v %) of 10 to 100 µg/ml concentration and applied as an disinfectant for disinfection of bird cages, experimental apparatuses, housings for domestic and laboratory animals, etc., by such procedures as dipping, coating or spraying.

The aforementioned Strain C-41206 and Strain C-41125, particularly C-41206, produce a compound of the formula [I] wherein R$_1$ is methyl, R$_2$ is methyl and X is

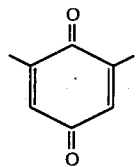

as well. In this specification, this compound is referred to as TAN-420F or briefly as F. Therefore, TAN-420F can be produced by cultivating a microorganism belonging to *Streptomyces hygroscopicus* subsp. tsukechiensis and capable of producing TAN-420F in a culture medium and harvesting TAN-420F so produced and accumulated in the culture. The cultivation of such microorganism and the recovery of said metabolite can be effected in the manner as described for TAN-420.

The physicochemical properties of TAN-420F as obtained in Example 2 which appears hereinafter are shown in Table 10.

TABLE 10

| | TAN-420F |
|---|---|
| Form | Yellow crystal |
| Melting point | >300° C. |
| Specific rotation | +245.8° (c = 0.5, CHCl$_3$) |
| Elemental analysis (%) | |
| C | 62.63 |
| H | 7.27 |
| N | 4.83 |
| Ultraviolet absorption spectrum $\lambda_{max}^{MeOH}$ | 271 nm (427), 396 nm (42.4) |
| Infrared absorption spectrum (main peak) $\nu_{max}^{KBr}$ | 1740, 1705, 1655, 1615, 1590, 1515, 1455, 1395, 1380, 1320, 1270, 1260, 1210, 1120, 1105, 1095, 1080, 1065, 1000, 925, 875, 850, 780, 745, 730, 700 |
| Thin layer chromatography Rf value | chloroform-methanol (9:1) 0.82    ethyl acetate-n-hexane (4:1) 0.50 |

TAN-420F is presumed to be the same compound as herbimycin A. It is known that herbimycin A has herbicidal activity [Journal of Antibiotics 32, 255–261 (1979), Tetrahedron Letters No. 44, 4323–4326 (1979)].

The present Antibiotic TAN-420 has herbicidal activity.

As the toxicity of the present Antibiotic TAN-420C, D and E are lower than that of herbimycin A, it is presumed that the toxicity of Antibiotic TAN-420 is lower than that of herbimycin A.

The following examples are further illustrative but by no means limitative of the invention.

EXAMPLE 1

*Streptomyces hygroscopicus* subsp. tsukechiensis No. C-41206 (IFO 14208, FERM BP-376) grown on a yeast extract-malt extract agar medium was used to inoculate a 200-ml Erlenmeyer flask including 40 ml of a seed culture medium containing 2% of glucose, 3% of soluble starch, 1% of soybean flour, 1% of corn steep liquor, 0.5% of peptone, 0.3% of NaCl and 0.5% CaCO$_3$ (pH 7.0) and incubated on a rotary shaker at 28° C. for 48 hours. A 5 ml portion of the preculture thus obtained was transferred to a 2000-ml Sakaguchi flask including 500 ml of the seed culture medium and incubated on a reciprocating shaker at 28° C. for 48 hours. This seed culture (500 ml) was further transferred to a 50-liter stainless steel tank including 30 l of the seed culture medium and incubated at 30 l/min. aeration, 280 r.p.m., 1 kg/cm² internal pressure and 28° C. for 48 hours. A 5-liter portion of the culture was transferred to a 200-liter stainless steel tank including 100 l of a fermentation medium containing 5% of mannitol, 3% of soybean flour, 0.1% of peptone, and 0.5% of CaCO₃ (pH 7.0) and incubated at 28° C., 100 l/min. aeration, 170 r.p.m. and 1 kg/cm² internal pressure for 114 hours.

A 100 l portion of the resulting culture was filtered with the aid of Hyflo-Supercel (Johns Manville, U.S.A.) and 94 l of the filtrate was extracted at pH 7.4 with two 47 l portions of ethyl acetate. The extracts were pooled and analyzed by thin-layer chromatography to confirm the presence of TAN-420D [Rf 0.70, chloroform-methanol (9:1)], TAN-420C [Rf 0.52, chloroform-methanol (9:1), TAN-420B [Rf 0.57, chloroform-methanol (9:1)], TAN-420A [Rf 0.17, chloroform-methanol (9:1)], TAN-420E [Rf 0.53, chloroform-methanol (9:1)], and TAN-420F [Rf 0.82, chloroform-methanol (9:1)].

For facilitating isolation of the desired compounds, TAN-420A and TAN-420C in the extract were oxidized to TAN-420B and TAN-420D and the entire extract was purified. Thus, the extract was washed with water and concentrated under reduced pressure to 18 l. The concentrate was stirred with 9 l of 2% (w/v) aqueous solution of ferric chloride. After 30 minutes, the ethyl acetate layer was washed twice with water and re-concentrated under reduced pressure to give 33 g of precipitates. The precipitates were subjected to chromatography on a column of silica gel (Kieselgel 60, Merck, 1.1 kg). After washing the column with 2 l of n-hexane, elution was carried out with n-hexane-ethyl acetate (1:1, 4 l→1:4, 3 l→1:9, 2 l) in the order mentioned. The fractions giving a substantially single spot of TAN-420D were pooled and concentrated to give 700 mg of TAN-420D as a yellow powder. The powder was further crystallized from ethyl acetate-n-hexane to give yellow crystals of TAN-420D. The fractions emerging prior to TAN-420D were pooled, concentrated, treated with a 2% aqueous solution of sodium hydrosulfite, concentrated, mixed with 100 g of silica gel and concentrated to dryness. The residue was applied to a column of 300 g silica gel and elution was carried out with chloroform (2 l), chloroform-methanol (50:1, 3 l), and chloroform-methanol (25:1, 5 l) in the order mentioned. Fractions containing TAN-420E were pooled, concentrated and crystallized from MeOH to give 22.5 g of TAN-420E as colorless crystals.

The mother liquor after recovery of the above precipitates was mixed with 80 g of silica gel, concentrated to dryness and applied to a column of 500 g silica gel. Elution was carried out with n-hexane (1 l) and then with n-hexane-ethyl acetate (2:1, 2 l→3:2, 3 l→1:1, 4 l→2:3, 4 l→1:2, 3 l→1:4, 2 l→and 1:9, 3 l) in the order mentioned.

Fractions predominantly composed of TAN-420B and TAN-420D were pooled, concentrated, mixed with 100 g of silica gel and concentrated to dryness. The residue was applied to a column of silica gel (600 g) and elution was carried out first with n-hexane (1 l) and then with chloroform (3 l) and chloroform-methanol (100:1, 4 l→50:1, 3 l→25:1, 3 l) in that order. Fractions predominantly composed of TAN-420D were pooled and concentrated. The residue was dissolved in ethyl acetate and reduced with a 2% aqueous solution of sodium hydrosulfite. The ethyl acetate layer was washed with water, dried and concentrated under reduced pressure to give 360 mg of TAN-420C as colorless crystalline powder. Concentration of fractions predominantly composed of TAN-420B yielded 100 mg of TAN-420B as yellow crystals.

EXAMPLE 2

A preculture was prepared by growing, in the manner of Example 1, *Streptomyces hygroscopicus* subsp. tsukechiensis No. C-41206 (IFO 14208, FERM BP-376) grown on a yeast extract-malt extract agar medium. The preculture obtained was transferred, in 0.5-ml portions, to 200-ml Erlenmeyer flasks each including 40 ml of fermentation medium and incubated on a rotary shaker at 28° C. for 114 hours. The resulting culture (3.0 liters) was filtered with Hyflo-Supercel, and the filtrate was adjusted to pH 7 and extracted with two portions of ethyl acetate. Thin layer chromatography revealed that the combined extract contained, as major components, TAN-420A, B, C, D and E [Rƒ value: 0.53 (developing solvent:chloroform-methanol (9:1)] and TAN-420F [Rƒ value: 0.82 (developing solvent:chloroform-methanol (9:1)]. The ethyl acetate extract was concentrated, mixed with 5 g of silica gel and again concentrated to dryness. The residue was placed on a silica gel (25 g) column and developed with 100 ml of n-hexane and then in sequence with chloroform and chloroform-methanol (100:1→50:1→25:1) mixed solvent systems. Those fractions that gave a single spot in TLC were pooled and concentrated to give 530 mg of colorless crystalline TAN-420E and 220 mg of yellow crystalline TAN-420F.

EXAMPLE 3

Preculture, seed culture and fermentation were conducted in the manner of Example 1 using *Streptomyces hygroscopicus* No. C-41125 (IFO 14207, FERM BP-375) grown on a yeast extract-malt extract agar medium. The resulting culture (70 liters), with Hyflo-Supercel added, was filtered, and the filtrate was adjusted to pH 7.0 and extracted with two 31-liter portinos of ethyl acetate. Thin layer chromatography revealed that the extract contained TAN-420E as the major component and furthermore TAN-420A, B, C, D and F.

The products were recovered from the extract and purified in the manner of Example 1 to give 82 mg of TAN-420B, 308 mg of TAN-420C, 283 mg of TAN-420D and 25 g of TAN-420E.

What we claim is:

1. A compound of the formula:

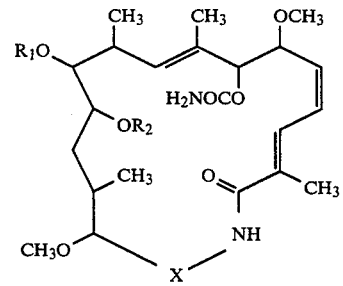

wherein $R_1$ and $R_2$ are the same or different and each represents hydrogen or methyl and X is

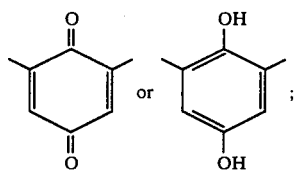

provided that when $R_1$ is hydrogen, $R_2$ is hydrogen or methyl and X is

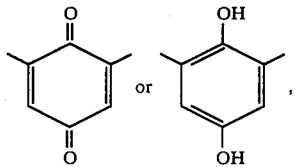

and when $R_1$ is methyl, $R_2$ is methyl and X is

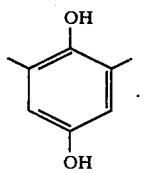

2. A compound as claimed in claim 1, wherein $R_1$ is hydrogen, $R_2$ is hydrogen and X is

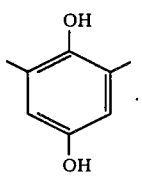

3. A compound as claimed in claim 1, wherein $R_1$ is hydrogen, $R_2$ is hydrogen and X is 4. A compound as claimed in claim 1, wherein $R_1$ is hydrogen, $R_2$ is methyl and X is

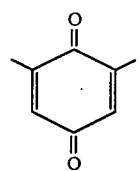

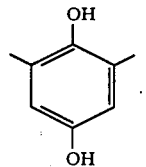

5. A compound as claimed in claim 1, wherein $R_1$ is hydrogen, $R_2$ is methyl and X is

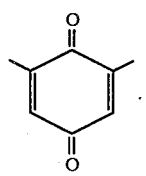

6. A compound as claimed in claim 1, wherein $R_1$ is methyl, $R_2$ is methyl and X is

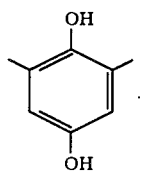

* * * * *